United States Patent [19]

Pettit

[11] Patent Number: 5,072,004

[45] Date of Patent: Dec. 10, 1991

[54] SYNTHETIC CONVERSION OF BRYOSTATIN 2 INTO BRYOSTATIN 1

[75] Inventor: George R. Pettit, Paradise Valley, Ariz.

[73] Assignee: Arizona Board of Regents acting on behalf of Arizona State University, Tempe, Ariz.

[21] Appl. No.: 636,212

[22] Filed: Dec. 31, 1990

[51] Int. Cl.$^5$ .............................................. C07D 493/22
[52] U.S. Cl. ................................................... 549/267
[58] Field of Search ......................................... 549/267

[56] References Cited

U.S. PATENT DOCUMENTS 4,560,774 12/1985 Pettit et al. ........................ 549/267
4,611,066  9/1986 Pettit et al. ........................ 549/267
4,833,257  5/1989 Pettit et al. ........................ 549/267

Primary Examiner—Bernard Dentz
Assistant Examiner—Amelia A. Owens
Attorney, Agent, or Firm—Richard R. Mybeck

[57] ABSTRACT

Bryostatin 2 is converted to bryostatin 1 by a selective protection and deprotection strategy involving the C-26 hydroxyl group.

5 Claims, No Drawings

SYNTHETIC CONVERSION OF BRYOSTATIN 2 INTO BRYOSTATIN 1

Some of the work described herein was funded by grants received from the National Institute of Health (CA 16049-07-12) awarded by the NCI and by the US army Medical Research and Developement Command (DAMD 17-89-Z-9021).

INTRODUCTION

Previous work at the Cancer Research Institute at Arizona State University, Tempe, Ariz. led to the discovery of several substances denominated Bryostatin 1, Bryostatin 2, Bryostatin 3 and others, which were found to possess, inter alia, varying degrees of therapeutic activity. These substances were each extracted from the marine *Bryozoam Bugula neritina.* One of the most potent of the bryostatins was bryostatin 1 although it was not necessarily the most prevalent. The present disclosure is predicated upon the discovery of an economically viable process of synthetically converting the less potent Bryostatin 2 into Bryostatin 1.

BACKGROUND OF THE INVENTION

The marine Bryozoam Bugula neritina was found to contain a series of biologically and chemically exciting constituents now known as the "bryostatins". Other interesting biosynthetic products of the Phylum Bryozoa such as the B-lactam bearing chartellines have recently been isolated from Chartella papyracea Bryostatin 1 has been found to profoundly effect protein kinase C and/or its isomers at less than picomolar concentrations and leads to powerful immunopotentiating activity. The ability of bryostatin 1 to initiate cytotoxic T-lymphocyte development, induce production of interleukin-2 and promote the growth of normal bone marrow cells combined with its strong antitumor and antineoplastic effect resulted in its selection for clinical development by the U.S. National Cancer Institute. In order to significantly increase the availability of bryostatin 1 it became very important to find a way to efficiently and selectively convert the equally prevalent but less active bryostatin 2, obtained from Bugula neritina in nearly equal amounts, to bryostatin 1. It is toward this goal that the present invention is directed.

BRIEF SUMMARY OF THE INVENTION

The present invention is based upon the discovery that Bryostatin 2 can be converted into Bryostatin 1 by selective protection and deprotection utilizing the C-26 hydroxyl group in the following fashion.

Bryostatin 2 is admixed with tert-butyldimethylsilyl chloride in the presence of 4-(N,N-dimethyl) aminopyridine and triethylamine in dimethylforamide at 25° C. for about 22 hours to form bryostatin 2, 26-tert-butyldimethylsilyl ether and bryostatin 2 7, 26-di-tert-butyldimethylsilyl ether. The bryostatin 2 26-tert-butyldimethylsilyl ether is then isolated and mixed with acetic/anhydride-pyridine at 25° C. for 18 hours to form bryostatin 2 26-tert-butyldimethylsilyl ether 7-acetate which is then mixed with 48% hydrofluoric acid-acetonitrile (1:20) at 0°-5° C. for 1.5 hours to yield bryostatin 1.

Accordingly a principal object of the present invention is to provide an economically viable alternative for the production of quantities of bryostatin 1 which are greater than that obtained by collecting and processing the marine *Bryozan Bugula nertitna.*

Another object of the present invention is to provide synthetic means and methods for converting less valuable stores of bryostatin 2 into more valuable bryostatin 1 which can be readily practiced with generally available laboratory equipment and reactants.

This and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

The bryostatin hydroxyl groups at C-3, C-9 and C-19 were earlier found to resist acetylation (under mild conditions), presumably due to intramolecular hydrogen bonding, while the C-7 and C-26 hydroxyl groups were readily acetylated. Thus synthetic conversion was undertaken by methods utilizing selective protection of the C-26 hydroxyl group. The steric environment of the two hydroxyl groups (viz, C-7 and C-26) suggested a bulky silyl ether would offer an attractive possibility.

Application of tert-butyldimethylsilyl chloride was found very effective for selective protection of the bryostatin 2 hydroxyl group at C-26. Bryostatin 2 was allowed to react at room temperature with excess tert-butyldimethylsilyl TBDMS) chloride in the presence of 4-(N,N-dimethyl) aminopyridine (and triethylamine in dimethylformamide) to produce the 26-tert-butyldimethylsilyl ether of bryostatin 2. The disilyl ether was reconverted to bryostatin 2 employing 48% hydrofluoric acidacetonitrile (1:20). The yield of monosilyl ether was 73.5% on the basis of total recovered bryostatin 2. Treatment of the C-26 silyl ether with acetic anhydride-pyridine (room temperature) gave the C-7 acetate. The C-26 hydroxyl was regenerated using 48% hydrofluoric acid-acetonitrile (1:20 at 0°-5° C.). This product thus obtained was isolated in 82d overall yield by silica gel column chromatography and found to be identical with natural bryostatin 1.

The high resolution SP-SIMS spectrum of bryostatin 1 displayed m/z 911 (M+Li)+ and 927 (M+Na)+ corresponding to the molecular formula $C_{47}H_{68}O_{17}$. The $^1$H NMR revealed an acetate chemical shift at 2.04, the C-7 proton at 5.14 dd, J=12, 4.9 Hz) and the three proton doublet of the C-27 methyl at δ 1.23 (J=6.5 Hz). The significant downfield shift of the C-7 proton from δ 6 3.95 to 5.14 further confirmed acetylation at the C-7 hydroxyl group.

Selective protection of the C-26 hydroxyl group in bryostatin 2 allowed the selective introduction of other groups at C-7. Treatment of 26-tert-butyldimethylsilyl ether OTBDMS with butyric anyhdride and pyridine, followed by deprotection, led to bryostatin 2 7-butyrate. Esterification of bryostatin 2 26-OTBDMS with isovaleric acid in the presence of dicyclohexylcarbodiimide and 4-(N,N-dimethyl)aminopyridine in methylene chloride provided the C-7 ester. Treatment of byrostatin 2 26-OTBDMS with pivalic anhydride and 4-(N,N-dimethyl)aminopyridine (50°-55° C.) in methylene chloride provided bryostatin 2 26-OTBDMS-7-pivalate Removal of the protecting group afforded byrostatin 2 7-pivalate in 42% overall yield.

To further aid in the understanding of the present invention and not by way of limitation the following examples are presented.

EXAMPLE I

General Procedures

Solvent solutions from reaction mixtures washed with water were dried over anhydrous sodium sulfate. All chromatographic solvents were redistilled. Commercial sources of silica gel (E. Merck, Darmstadt, 70–230 mesh) were employed for column chromatography and silica gel GHLF uniplates (Analtech, Inc., Newark, Del.) were used for thin layer chromatography TLC). The TLC plates were viewed with UV light and developed with anisaldehyde-sulfuric acid spray reagent followed by heating. The NMR spectra were measured using a Eruker AM-400 instrument with deuteriochloroform employed as solvent. All high and low resolution fast atom bombardment (FAB) mass spectra were recorded using a Kratos MS-50 mass spectrometer Mid West Center for Mass Spectrometry, University of Nebraska, Lincoln, Nebr.).

EXAMPLE II

Conversion of Bryostatin 2 to Bryostatin 2 26-tert-butyldimethylsilyl ether

The following procedure for silyation, acylation and desilyation was repeated in analogous fashion for each bryostatin interconversion. A solution of bryostatin 2 (50 mg), 4-(N,N dimethyl)aminopyridine 15 mg), tert-butyldimethylsilyl chloride (40 mg) and trimethylamine (20 µl) in dimethylformamide (2 ml) was stirred at room temperature (under argon) for 22 hours. The reaction mixture was diluted with ice water, stirred for 10 minutes and extracted with methylene chloride. The organic phase was washed with saturated aqueous sodium bicarbonate, followed by water, dried, and solvent evaporated under reduced pressure. The residue was purified by column chromatography on silica gel (1:1 hexane-ethyl acetate) to afford silyl ether (21.8 mg), bryostatin 2 7 26-di-tert butyldimethylsilyl ether 21.4 mg). and bryostatin 2 (5.5 mg). The disilylated product protection was removed with 48% hydrofluoric acid-acetonitrile (1:20, 10 ml). The reaction mixture was stirred at 0°-5° C. (1.5 h), diluted with water, and extracted with methylene chloride . The chlorocarbon phase was washed with saturated aqueous sodium bicarbonate followed by water and dried. The residue from solvent removal at reduced pressure) was separated by silica gel column chromatography 1:1 hexane-ethyl acetate) to afford 17.2 mg of bryostatin 2. On the basis of total recovered bryostatin 2 the yield of monosilyl ether was 73.5%. The 400-MHz $^1$H NMR spectrum of silyl ether displayed significant chemical shifts at δ 0.07 (s. 3H), 0.11 (s, 3H), 0.90 (s, 9H), 1.08 (d, 3H, J=5.6 Hz), 3.65 (s, 3H), 3.68 (s, 3H), 3.73 m. 1H) and 3.95 (m, 1H).

EXAMPLE III

Conversion of Bryostatin 2 26-tert-butyldimethylsilyl ether to Bryostatin 1

A solution of bryostatin 2 26-tert-butyldimethylsilyl ether (1.6 mg) in acetic anhydride (100 µL) - pyridine (150 µL) was stirred for 18 h (room temperature), diluted with methanol and stirred an additional 30 min. Solvent was removed (reduced pressure) and the residue was chromotographed on a column of silica gel (1:1 hexane-ethyl acetate) to afford 1.2 mg (72%) of acetate. The product was subjected to desilylation by treating with 48% hydrofluoric acid-acetonitrile (1:20, 100 µL). The reaction mixture was stirred at 0°-5° C. (1.5 h), diluted with water and extracted with methylene chloride. The organic phase was washed with saturated aqueous sodium bicarbonate and water and dried. The residue from solvent removal (reduced pressure) was purified by silica gel column chromatography (1:1 hexane-ethyl acetate) to afford bryostatin 1 (0.8 mg, 80%) identical with the natural product (by comparison TLC, analytical HPLC, SP-SIMS and $^1$H NMR).

From the foregoing, it is readily apparent that a new and useful synthetic conversion of bryostatin 2 into bryostatin 1 has been herein described and illustrated which fulfilles all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

What is claimed is:

1. The synthetic conversion of bryostatin 2 into bryostatin 1 comprising: admixing bryostatin 2 with tert-butyldimethylsilyl chloride in the presence of 4-(N,N-dimethylaminopyridine and triethylamine in dimethylformamide at 25° C. for about 22 hours to form a product containing byrostatin 2 26-tert-butyldimethylsilyl ether and bryostatin 2 7, 26-di-tert -butyldimethylsilyl ether; isolating said bryostatin 2 26 - tert - butyldimethylsilyl ether from said product; mixing said isolated bryostatin 2 26-tert-butyldimethylsilyl ether with acetic anhydride-pyridine at 25° C. for 18 hours to form bryostatin 2, 26 -tert-butyldimethylsilyl ether 7-acetate; mixing said 2 26-tert-butyldimethylsilyl ether 7-acetate with 48% hydrofluoric acid-acetonitrile (1:20) at 0°-5° C. for 1.5 hours to form bryostatin 1; and collecting said bryostatin 1.

2. The method of producing bryostatin 1 comprising the steps of converting bryostatin 2 to bryostatin 2 26-tert-butyldimethylsilyl ether and therafter converting bryostatin. 2 26-tert-butyldimethylsilyl ether to bryostatin 1.

3. The method according to claim 2 in which said bryostatin 2 is converted to bryostatin 2 26-tert-butyldimethylsilyl ether by admixing said bryostatin 2 with tert-butyldimethylsilyl chloride in the presence of 4-(N,N-dimethyl) aminopyridine and triethylamine in dimethylforamide.

4. The method according to claim 3 in which said byrostatin 2 26-tert-butyldimethylsilyl ether is converted to bryostatin 2, 26 -tert-butyldimethylsilyl ether 7-acetate) mixing said bryostatin 2 26-tert-butaldimethylsilyl ether 7-acetate with 48% hydrofluoric acid-acetonitrile (1:20) at 0°-5° C. for 1.5 hours to form bryostatin 1; and collecting said bryostatin 1.

5. The method according to claim 3 in which said byrostatin 2 26-tert-butyldimethylsilyl ether is converted to bryostatin 2, 26 -tert-butyldimethylsilyl ether 7-acetate; mixing said bryostatin 2 26-tert-butaldimethylsilyl ether 7-acetate with 48% hydrofluoric acid-acetonitrile (1:20).

* * * * *